United States Patent
Zussman

(10) Patent No.: US 9,297,094 B2
(45) Date of Patent: Mar. 29, 2016

(54) USE OF ELECTROSPUN MICROTUBES FOR DRUG DELIVERY

(75) Inventor: Eyal Zussman, Haifa (IL)

(73) Assignee: TECHNION RESEARCH & DEVELOPMENT FOUNDATION LTD., Haifa (IL)

(*) Notice: Subject to any disclaimer, the term of this patent is extended or adjusted under 35 U.S.C. 154(b) by 0 days.

(21) Appl. No.: 12/918,377

(22) PCT Filed: Feb. 12, 2009

(86) PCT No.: PCT/IL2009/000170
§ 371 (c)(1),
(2), (4) Date: Oct. 12, 2010

(87) PCT Pub. No.: WO2009/104175
PCT Pub. Date: Aug. 27, 2009

(65) Prior Publication Data
US 2011/0028834 A1 Feb. 3, 2011

Related U.S. Application Data

(60) Provisional application No. 61/064,210, filed on Feb. 21, 2008, provisional application No. 61/064,206, filed on Feb. 21, 2008, provisional application No. 61/064,204, filed on Feb. 21, 2008.

(51) Int. Cl.
*A61M 25/00* (2006.01)
*D01D 5/00* (2006.01)
(Continued)

(52) U.S. Cl.
CPC .............. *D01D 5/003* (2013.01); *A61K 9/0092* (2013.01); *B82Y 30/00* (2013.01); *C02F 3/102* (2013.01);
(Continued)

(58) Field of Classification Search
CPC ......... A61K 9/00; A61K 9/48; A61K 9/4816; A61K 9/50; A61K 9/5005; D01D 5/003; D01D 5/0038; D01D 5/0046; D01D 5/0084; D01D 5/247

USPC ............ 604/523, 500, 93.01, 164.01–170.03, 604/158–163, 257, 288.02; 264/464, 465; 600/431
See application file for complete search history.

(56) References Cited

U.S. PATENT DOCUMENTS 4,921,475 A * 5/1990 Sibalis ........................... 604/20
5,209,734 A * 5/1993 Hurley et al. ................. 604/158
(Continued)

FOREIGN PATENT DOCUMENTS

| AU | 2007303821 | 4/2008 |
|---|---|---|
| CN | 1799649 | 7/2006 |

(Continued)

OTHER PUBLICATIONS

McCann et al. Electrospinning of nanofibers with core-sheath, hollow, or porous structures. Journal of Materials Chemistry, 2005: pp. 735-738.*

(Continued)

*Primary Examiner* — Laura Bouchelle
(74) *Attorney, Agent, or Firm* — The Roy Gross Law Firm, LLC; Roy Gross

(57) ABSTRACT

Provided is a method of delivering a medicament or a diagnostic agent to a subject in need thereof by (a) introducing a microtube configured to deliver the medicament or the diagnostic agent into the subject, said microtube comprises an electrospun shell and an electrospun coat over an internal surface of said shell, and (b) administering the medicament or the diagnostic agent through said microtube, thereby delivering the medicament or the diagnostic agent to the subject. Also provided are kits for delivering a medicament or a diagnostic agent.

28 Claims, 6 Drawing Sheets

(51) Int. Cl.
*A61K 9/00* (2006.01)
*B82Y 30/00* (2011.01)
*C02F 3/10* (2006.01)
*C02F 3/34* (2006.01)
*D01D 5/247* (2006.01)
*D01F 1/10* (2006.01)
*D01F 8/14* (2006.01)
*G01N 33/543* (2006.01)
*C02F 101/18* (2006.01)
*C02F 101/20* (2006.01)
*C02F 101/30* (2006.01)
*C02F 101/36* (2006.01)

(52) U.S. Cl.
CPC . *C02F 3/34* (2013.01); *C02F 3/342* (2013.01); *D01D 5/247* (2013.01); *D01F 1/10* (2013.01); *D01F 8/14* (2013.01); *G01N 33/54393* (2013.01); *C02F 2101/18* (2013.01); *C02F 2101/20* (2013.01); *C02F 2101/306* (2013.01); *C02F 2101/36* (2013.01); *C02F 2305/08* (2013.01); *Y02W 10/15* (2015.05); *Y10T 428/1393* (2015.01)

(56) References Cited

U.S. PATENT DOCUMENTS

| | | | |
|---|---|---|---|
| 5,688,501 | A | 11/1997 | Merril et al. |
| 5,795,340 | A * | 8/1998 | Lang ............................. 604/533 |
| 6,537,195 | B2 * | 3/2003 | Forman .............................. 600/3 |
| 6,537,241 | B1 * | 3/2003 | Odland ............................. 604/9 |
| 7,066,922 | B2 * | 6/2006 | Angel et al. ................... 604/500 |
| 2001/0014394 | A1 * | 8/2001 | Soane et al. ................... 428/364 |
| 2001/0034503 | A1 * | 10/2001 | Mehier .......................... 604/158 |
| 2003/0098518 | A1 * | 5/2003 | Averdung et al. ............... 264/10 |
| 2003/0135158 | A1 * | 7/2003 | Gonnelli ........................ 604/140 |
| 2003/0139727 | A1 * | 7/2003 | Angel et al. ................... 604/506 |
| 2004/0018226 | A1 * | 1/2004 | Wnek et al. .................... 424/443 |
| 2004/0030377 | A1 * | 2/2004 | Dubson et al. ............... 623/1.13 |
| 2004/0147903 | A1 * | 7/2004 | Latini ............................ 604/523 |
| 2004/0223954 | A1 | 11/2004 | Bruessow et al. |
| 2005/0180992 | A1 | 8/2005 | Belcher et al. |
| 2006/0119015 | A1 | 6/2006 | Wehrspohn et al. |
| 2006/0200232 | A1 * | 9/2006 | Phaneuf et al. .............. 623/1.42 |
| 2006/0226580 | A1 * | 10/2006 | Xia et al. ....................... 264/465 |
| 2006/0228435 | A1 * | 10/2006 | Andrady et al. ........ 425/174.8 R |
| 2009/0061496 | A1 | 3/2009 | Kuhn et al. |
| 2010/0129656 | A1 | 5/2010 | Zussman et al. |
| 2010/0303881 | A1 | 12/2010 | Hoke et al. |
| 2011/0081394 | A1 | 4/2011 | Zussman et al. |

FOREIGN PATENT DOCUMENTS

| | | |
|---|---|---|
| EP | 2079860 | 7/2009 |
| WO | WO 03/000381 | 1/2003 |
| WO | WO 2006/019293 | 2/2006 |
| WO | WO 2006/108809 | 10/2006 |
| WO | WO 2008/041183 | 4/2008 |
| WO | WO 2009/104174 | 8/2009 |
| WO | WO 2009/104175 | 8/2009 |
| WO | WO 2009/104176 | 8/2009 |

OTHER PUBLICATIONS

International Preliminary Report on Patentability Dated Apr. 16, 2009 From the International Bureau of WIPO Re.: Application No. PCT/IB2007/054001.
International Search Report and the Written Opinion Dated Sep. 29, 2009 From the International Searching Authority Re.: Application No. PCT/IL2009/000169.
International Search Report and the Written Opinion Dated Sep. 29, 2009 From the International Searching Authority Re.: Application No. PCT/IL2009/000171.
International Search Report and the Written Opinion Dated Sep. 30, 2009 From the International Searching Authority Re.: Application No. PCT/IL2009/000170.
International Search Report Dated Oct. 14, 2008 From the International Searching Authority Re.: Appliation No. PCT/IB2007/054001.
Written Opinion Dated Oct. 14, 2008 From the International Searching Authority Re.: Application No. PCT/IB2007/054001.
Bognitzki et al. "Polymer, Metal, and Hybrid Nano- and Mesotubes by Coating Degradable Polymer Template Fibers (TUFT Process)", Advanced Materials, 12(9): 637-640, 2000.
Caruso et al. "Titanium Dioxide Tubes From Sol-Gel Coating of Electrospun Polymer Fibers", Advanced Materials, 13: 1577-1579, Oct. 16, 2001.
Dror et al. "One-Step Production of Polymeric Microtubes by Co-Electrospinning", Small, XP002497054, 3(6): 1064-1073, Jun. 4, 2007.
Huang et al. "Encapsulating Drugs in Biodegradable Ultrafine Fibers Through Co-Axial Electrospinning", Journal of Biomedical Materials Research, Part A, 77A: 169-179, 169, 2006.
Jiang et al. "A Facile Technique to Prepare Biodegradable Coaxial Electrospun Nanofibers for Controlled Release of Bioactive Agents", Journal of Controlled Release, XP005163067, 108(2-3): 237-243, Nov. 28, 2005.
Jiang et al. "Modulation of Protein Release From Biodegradable Core-Shell Structured Fibers Prepared by Coaxial Electrospinning", Journal of Biomedical Materials Research Part B: Applied Biomaterials, 79B: 50-57, 2006.
Li et al. "Direct Fabrication of Composite and Ceramic Hollow Nanofibers by Electrospinning", Nano Letters, 4(5): 933-938, 2004.
Li et al. "Electrospinning of Nanofibers: Reinventing the Wheel?", Advanced Materials, 16(14): 1151-1170, Jul. 19, 2004.
Li et al. "Electrospinning: A Simple and Versatile Technique for Producing Ceramic Nanofibers and Nanotubes", Journal of the American Ceramic Society, 89(6): 1861-1869, 2006.
Li et al. "Use of Electrospinning to Directly Fabricate Hollow Nanofibers With Functionalized Inner and Outer Surfaces", Small, XP002497053, 1(1): 83-86, Jan. 1, 2005.
Loscertales et al. "Electrically Forced Coaxial Nanojets for One-Step Hollow Nanofiber Design", Journal of the American Chemical Society, JACS, 126: 5376-5377, 2004.
Loscertales et al. "Micro/Nano Encapsulation Via Electrified Coaxial Liquid Jets", Science, 295: 1695-1698, Mar. 16, 2002.
Reneker et al. "Electrospinning of Nanofibers From Polymer Solutions and Melts", Advances in Applied Mechanics, 41: 1-3, 103-115, 142-153, 2006.
Reznik et al. "Evolution of a Compound Droplet Attached to a Core-Shell Nozzle Under the Action of a Strong Electric Field", Physics of Fluids, 18: 062101-1-062101-13, 2006.
Salalha et al. "Encapsulation of Bacteria and Viruses in Electrospun Nanofibres", Nanotechnology, 17: 4675-4681, 2006.
Sun et al. "Compound Core-Shell Polymer Nanofibers by Co-Electrospinning", Advanced Materials, XP002497055, 15(22: 1929-1932, Nov. 17, 2003.
Xie et al. "Ultra-High Surface Fibrous Membranes From Electrospinning of Natural Proteins: Casein and Lipase Enzyme", Journal of Materials Science, 38: 2125-2133, 2003.
Yarin et al. "Material Encapsulation and Transport in Core-Shell Micro/Naonofibers, Polymer and Carbon Nanotubes and Micro/Nanochannels", Journal of Materials Chemistry, XP002546457, 17(25): 2585-2599, Jul. 1, 2007. Chapter III Section (ii).
Yu et al. "Production of Submicrometer Diameter Fibers by Two-Fluid Electrospinning", Advanced Materials, 16(17): 1562-1566, Sep. 3, 2004.
Zussman et al. "Electrospun Polyacrylonitrile/Poly(Methyl Methacrylate)-Derived Turbostratic Carbon Micro-/Nanotubes", Advanced Materials, 18: 348-353, 2006.
Official Action Dated Feb. 14, 2012 From the US Patent and Trademark Office Re. U.S. Appl. No. 12/311,601.
Response Dated Feb. 1, 2011 to Official Action of Oct. 1, 2010 From the US Patent and Trademark Office Re. U.S. Appl. No. 11/896,130.
Restriction Official Action Dated May 9, 2012 From the US Patent and Trademark Office Re. U.S. Appl. No. 12/918,372.
Official Action Dated Nov. 3, 2011 From the US Patent and Trademark Office Re. U.S. Appl. No. 11/896,130.
International Preliminary Report on Patentability Dated Sep. 2, 2010 From the International Bureau of WIPO Re. Application No. PCT/IL2009/000171.

(56) References Cited

OTHER PUBLICATIONS

International Preliminary Report on Patentability Dated Sep. 2, 2010 From the International Bureau of WIPO Re.: Application No. PCT/IL2009/000169.
International Preliminary Report on Patentability Dated Sep. 2, 2010 From the International Bureau of WIPO Re.: Application No. PCT/IL2009/0001790.
Communication Pursuant to Article 94(3) EPC Dated Dec. 2011 From the European Patent Office Re. Application No. 07826621.0.
Restriction Official Action Dated Dec. 23, 2011 From the US Patent and Trademark Office Re. U.S. Appl. No. 12/311,601.
Official Action Dated Oct. 1, 2010 From the US Patent and Trademark Office Re. U.S. Appl. No. 11/896,130.
Lee et al. "Virus-Based Fabrication of Micro- and Nanofibers Using Electrospinning", NanoLetters, 4(3): 387-390, 2004.
Salalha et al. "Encapsulation of Bacteria and Viruses in Electrospun Nanofibres", Nanotechnology, 17: 4675-4681, Aug. 30, 2006.
Theron et al. "Electrostatic Field-Assisted Alignment of Electrospun Nanofibres", Nanotechnology, 12: 384-390, 2001.
Response Dated Mar. 24, 2011 to Office Action of Oct. 13, 2010 From the State Intellectual Property Office of the People's Republic of China Re. Application No. 200780044536.1.
Official Action Dated Apr. 7, 2011 From the US Patent and Trademark Office Re. U.S. Appl. No. 11/896,130.
Zussman et al. "Formation of Nanofiber Crossbar in Electrospinning", Applied Physics Letters, 82(6): 973-975, Feb. 10, 2003.
Response Dated Aug. 2, 2011 to Official Action of Apr. 7, 2011 From the US Patent and Trademark Office Re. U.S. Appl. No. 11/896,130.
Larsson et al. "Detection of Number and Viability of E. Coli and A. Hydrophila With FISH Technique", Techneau, D.3.5.3, p. 1-30, Apr. 30, 2008.
Translation of Office Action Dated Mar. 1, 2012 From the State Intellectual Property Office of the People's Republic of China Re. Application No. 200780044536.1.
Translation of Office Action Dated Oct. 13, 2010 From the State Intellectual Property Office of the People's Republic of China Re. Application No. 200780044536.1.
He et al. "Recent Development of the Nanocomposites Prepared by Coaxial Jet Technology", Acta Materiae Compositae Sinica, 22(6): 1-8, Dec. 2005. Abstract in English.
Li et al. "Porous Ultrafine Nanofibers Having a Ultrahigh Specific Surface Area", Chinese Science Bulletin, 49(21): 2160-2163, Nov. 2004. Chinese Only!
Translation of Office Action Dated Dec. 4, 2012 From the State Intellectual Property Office of the People's Republic of China Re. Application No. 200780044536.1.
Official Action Dated Feb. 2013 From the US Patent and Trademark Office Re. U.S. Appl. No. 12/311,601.
Patent Examination Report Dated Nov. 19, 2012 From the Australian Government, IP Australia Re. Application No. 2007303821.
Restriction Official Action Dated May 9, 2012 From the US Patent and Trademark Office Re. U.S. Appl. No. 12/918,365.
Restriction Official Action Dated Mar. 1, 2013 From the US Patent and Trademark Office Re. U.S. Appl. No. 12/918,365.
Communication Pursuant to Article 94(3) EPC Dated Jul. 18, 2012 From the European Patent Office Re. U.S. Appl. No. 09713280.7.
Communication Pursuant to Article 94(3) EPC Dated Jul. 19, 2012 From the European Patent Office Re. Application No. 09712148.7.
Communication Pursuant to Article 94(3) EPC Dated Jul. 19, 2012 From the European Patent Office Re. Application No. 09713264.1.
Official Action Dated Aug. 8, 2012 From the US Patent and Trademark Office Re. U.S. Appl. No. 12/918,372.
Official Action Dated Aug. 17, 2012 From the US Patent and Trademark Office Re. U.S. Appl. No. 12/311,601.
Communication Under Rule 71(3) EPC Dated Mar. 5, 2013 From the European Patent Office Re. Application No. 07826621.0.
Decision to Grant a European Patent Pursuant to Article 97(1) EPC Dated Jul. 11, 2013 From the European Patent Office Re. Application No. 07826621.0.
Dror et al. "Encapsulation of Enzymes in Biodegradable Tubular Structures", Macromolecules, 41(12): 4187-4192, May 24, 2008.
Communication Pursuant to Article 94(3) EPC Dated Aug. 20, 2013 From the European Patent Office Re. Application No. 09713264.1.
Official Action Dated Jan. 17, 2014 From the US Patent and Trademark Office Re. U.S. Appl. No. 12/918,365.
Advisory Action Before the Filing of an Appeal Brief Dated May 30, 2014 From the US Patent and Trademark Office Re. U.S. Appl. No. 12/918,365.
Requisition Dated May 22, 2014 From the Canadian Intellectual Property Office Re. Application No. 2,664,972.
Communication Pursuant to Article 94(3) EPC Dated Aug. 23, 2013 From the European Patent Office Re. Application No. 09713280.7.
Official Action Dated Sep. 6, 2013 From the US Patent and Trademark Office Re. U.S. Appl. No. 12/918,372.
Official Action Dated Oct. 1, 2014 From the US Patent and Trademark Office Re. U.S. Appl. No. 11/896,130.
Dror et al. "Viable Encapsulation of Enzymes in Biodegradable Tubular Structures", Faculty of Mechanical Engineering, Faculty of Biology, Technion, Israel Institute of Technology, Haifa, IL, 18 P, May 24, 2008.
Li et al. "Nano-Porous Ultra-High Specific Surface Ultrafine Fibers", Chinese Science Bulletin, 49(22): 2368-2371, Nov. 2004.
Advisory Action Before the Filing of an Appeal Brief Dated Apr. 12, 2013 From the US Patent and Trademark Office Re. U.S. Appl. No. 12/311,601.
Advisory Action Before the Filing of an Appeal Brief Dated May 16, 2013 From the US Patent and Trademark Office Re. U.S. Appl. No. 12/311,601.
Official Action Dated Jun. 18, 2013 From the US Patent and Trademark Office Re. U.S. Appl. No. 12/918,365.
Translation of Office Action Dated Jun. 4, 2013 From the State Intellectual Property Office of the People's Republic of China Re. Application No. 200780044536.1.
Applicant-Initiated Interview Summary Dated Apr. 30, 2014 From the US Patent and Trademark Office Re. U.S. Appl. No. 12/918,372.
Official Action Dated Mar. 11, 2013 From the US Patent and Trademark Office Re. U.S. Appl. No. 12/918,372.
Kim et al. "Controlled Protein Release From Electrospun Biodegradable Fiber Mesh Composed of Poly(Epsilon-Caprolactone) and Poly(Ethylene Oxide)", International Journal of Pharmaceutics, 338: 276-283, 2007.
Zhang et al. "Biomimetic and Bioactive Nanofibrous Scaffolds From Electrospun Composite Nanofibers", International Journal of Nanomedicine, 2(4): 623-638, 2007.
Communication Under Rule 71(3) EPC Dated Dec. 10, 2013 From the European Patent Office Re. Application No. 09712148.7.
Office Action Dated Nov. 21, 2013 From the State Intellectual Property Office of the People's Republic of China Re. Application No. 200780044536.1 and Its Translation into English.
Official Action Dated Jan. 14, 2015 From the US Patent and Trademark Office Re. U.S. Appl. No. 12/311,601.
Applicant-Initiated Interview Summary Dated Jul. 29, 2015 From the US Patent and Trademark Office Re. U.S. Appl. No. 12/918,372.
Official Action Dated Feb. 5, 2015 From the US Patent and Trademark Office Re. U.S. Appl. No. 12/918,372.
Official Action Dated Oct. 6, 2015 From the US Patent and Trademark Office Re. U.S. Appl. No. 12/918,372.
Official Action Dated Oct. 8, 2015 From the US Patent and Trademark Office Re. U.S. Appl. No. 12/918,365.
Official Action Dated Feb. 4, 2015 From the US Patent and Trademark Office Re. U.S. Appl. No. 12/918,365.
Requisition and Examination Search Report Dated Jan. 23, 2015 From the Canadian Intellectual Property Office Re. Application No. 2,664,972.
Interantional Preliminary Report on Patentability Dated Sep. 2, 2010 From the International Bureau of WIPO Re. Application No. PCT/IL2009/000171.
Zhang et al. "Coaxial Electrospinning of (Fluorescein Isothiocyanate-Conjugated Bovine Serum Albumin)-Encapsulated Poly($\epsilon$-Caprolactone) Nanofibers for Sustained Release", Biomacromolecules, 7(4): 1049-1057, 2006.

* cited by examiner

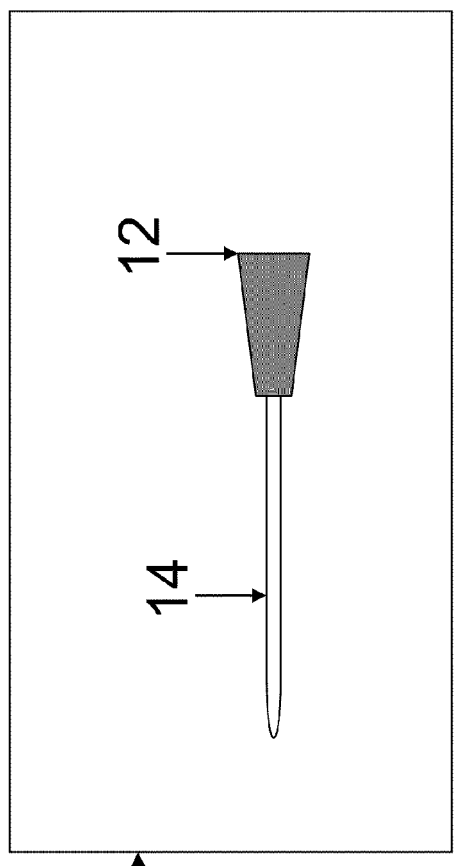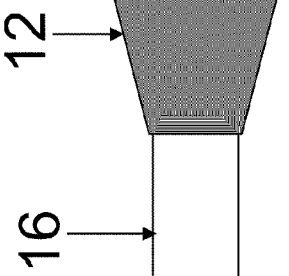
FIG. 3A
FIG. 3B

USE OF ELECTROSPUN MICROTUBES FOR DRUG DELIVERY

RELATED APPLICATIONS

This Application is a National Phase of PCT Patent Application No. PCT/IL2009/000170 having International filing date of Feb. 12, 2009, which claims the benefit of U.S. Provisional Patent Application Nos. 61/064,210, 61/064,206 and 61/064,204 filed on Feb. 21, 2008.

The teachings of PCT/IB2007/054001 are incorporated herein by reference.

The contents of all of the above documents are incorporated by reference as if fully set forth herein.

FIELD AND BACKGROUND OF THE INVENTION

The present invention, in some embodiments thereof, relates to a method of delivering a medicament (e.g., a drug) or a diagnostic agent to a subject and, more particularly, but not exclusively, to an implantable drug delivery device.

Drugs are designed to provide a therapeutic effect on diseased or damaged cell type(s) or tissue(s). However, occasionally, due to lack of cell specificity, limited solubility and/or poor distribution of the drug, high doses of drug molecules are needed to achieve a therapeutic effect on cells of a tissue-of-interest. In spite of being expensive, administering of high drug concentrations may be deleterious to the non-target cells/tissues. For example, treating of small cell lung cancer with systemic administration of chemotherapy drugs (e.g., cisplatin and etoposide) is associated with side effects such as hair loss, sickness (nausea), fatigue, diarrhea, mouth ulcers and anemia. In addition, most drugs and carriers (e.g., polymers, liposomes, emulsions, micro and nanoparticles) have limited capacity of penetrating the blood-brain barrier.

Magnetic resonance imaging (MRI), X-ray imaging including computed tomography (CT) as well as radiography and fluoroscopy, are the most widely used modalities in modern medical imaging. The contrast agents used for CT and MRI include small (e.g., less than 1 kDa) molecular contrast media (SMCM) such as Gd-DTPA [a complex of gadolinium with a chelating agent (diethylenetriamine penta-acetic acid; DTPA)], Gd-DTPA-BMA, Gd-DOTA, diatrizoate, Iohexol, Iopamidol Iodixano, or large macromolecules contrast media (MMCM) with a blood pool, intravascular distribution (see for example, U.S. Patent Application No. 20070248547). For bone scan, radioactive tracers such as technezium and radioactive iodine ($I^{123}$) are used. However, the exposure of the whole body (e.g., via intravenous administration) to such agents can be associated with undesired side effects (e.g., nausea, dizziness) and can also result in long-term damage to healthy cells (e.g., increase the risk to cancer).

Various means for delivery of a drug to a tissue-of-interest are available. For example, drugs can be administered via a central line (i.e., a tube which is inserted under the skin into a vein above the heart), a catheter (e.g., for abdominal injection of chemotherapy in ovarian cancer), a needle or an implanted drug reservoir with injection means (e.g., a catheter with an infusion or mechanic pump). In addition, the Percutaneous Hepatic Perfusion (PHP) system (Delcath system, NY, USA), composed of catheters and filters, was developed for administering chemotherapy to the liver. It infuses the drug directly to the liver via the hepatic artery, filters the venous effluent from the liver outside of the body and returns the filtered blood to the jugular vein.

Fabrication of nanoscopic and microscopic hollow structures such as polymer tubes receives increasing attention due to the potential application of tubes in drug release.

U.S. Pat. Appl. No. 20060142466 discloses a polymer-carbon nanotube material for drug delivery.

The electrospinning process is well-known for producing nanofibers and polymeric nanofibers in particular (Reneker D H., et al., 2006; Ramakrishna S., et al., 2005; Li D, et al., 2004; PCT WO 2006/106506 to the present inventor).

Methods of fabricating tubes by electrospinning include the TUFT process (Bognitzki et al. 2000) which uses the electrospun nanofibers as templates; the modification of the TUFT process using the sol-gel procedure (Caruso et al., 2001); co-electrospinning of two different solutions to produce core-shell nanofibers (Sun Z, et al., 2003; Yu J H, et al., 2004; Huang Z M, et al., 2006; Jiang H., et al., 2005; Zhang Y Z., et al., 2006) followed by the selective removal of the core (Li D., et al., 2004; Li D., et al., 2005; Zussman E, et al., 2006); and production of hollow fibers by introducing a liquid containing a polymer to a porous template material, and removal of the template following polymer solidification (US patent application No. 20060119015 to Wehrspohn R., et al.).

Studies show that co-electrospinning of two polymeric solutions which are sufficiently viscous, spinnable and immiscible can result in solid core-shell fibers (i.e., filled fibers and not hollow fibers) (Li D., et al., 2006; Loscertales I G., et al., 2002; Loscertales I G., et al., 2004). Sun Z et al. (2003) showed that although core-shell nanofibers made of miscible solutions can be achieved this process is less controllable since mutual diffusion can take place in the Taylor cone and during the jet stretching.

PCT/IB2007/054001 to the present inventor (which is fully incorporated herein by reference) discloses methods of producing electrospun microtubes (i.e., hollow fibers) which can be further filled with liquids and be used as microfluidics.

SUMMARY OF THE INVENTION

According to an aspect of some embodiments of the present invention there is provided a kit for delivering a medicament or a diagnostic agent, comprising: (i) a coupling element, and (ii) an infusion microtube which comprise an electrospun shell and an electrospun coat over an internal surface of the shell.

According to an aspect of some embodiments of the present invention there is provided a kit for delivering a medicament or a diagnostic agent, comprising: (i) a reservoir which comprises the medicament, and (ii) an infusion microtube which comprise an electrospun shell and an electrospun coat over an internal surface of the shell.

According to an aspect of some embodiments of the present invention there is provided a method of delivering a medicament or a diagnostic agent to a subject in need thereof, comprising: (a) introducing a microtube configured to deliver the medicament or the diagnostic agent into the subject, the microtube comprises an electrospun shell and an electrospun coat over an internal surface of the shell; and (b) administering the medicament or the diagnostic agent through the microtube, thereby delivering the medicament or the diagnostic agent to the subject.

According to some embodiments of the invention, the microtube is attached to a coupling element.

According to some embodiments of the invention, the microtube is connected to a reservoir which comprises the medicament or the diagnostic agent.

According to some embodiments of the invention, the reservoir is connected to a pump.

According to some embodiments of the invention, the reservoir is connected to or comprises a filter.

According to some embodiments of the invention, the coupling element is attached to the infusion microtube.

According to some embodiments of the invention, the kit further comprising a reservoir which comprises the medicament or the diagnostic agent.

According to some embodiments of the invention, the reservoir is connected to the coupling element.

According to some embodiments of the invention, the kit further comprises a pump.

According to some embodiments of the invention, the kit further comprises a filter.

According to some embodiments of the invention, the kit further comprising a coupling element attached to the infusion microtube.

According to some embodiments of the invention, the coupling element is connected to the reservoir.

According to some embodiments of the invention, the microtube is produced by co-electrospinning two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution.

According to some embodiments of the invention, step (b) of the method is effected prior to step (a).

According to some embodiments of the invention, step (b) of the method is effected following step (a).

According to some embodiments of the invention, introducing is effected by implanting the microtube in a subject in need thereof.

According to some embodiments of the invention, the implanting is effected at or in proximity to a tissue-of-interest.

According to some embodiments of the invention, the administering is effected via an opening of the microtube.

According to some embodiments of the invention, the reservoir is an implantable reservoir.

According to some embodiments of the invention, the reservoir is attached on a skin of the subject in need thereof.

According to some embodiments of the invention, the medicament comprises a drug.

According to some embodiments of the invention, the drug is soluble in an aqueous solution.

According to some embodiments of the invention, the electrospun shell is formed of a first polymeric solution and the electrospun coat is formed of a second polymeric solution.

According to some embodiments of the invention, the first polymeric solution solidifies faster than the second polymeric solution.

According to some embodiments of the invention, a solvent of the second polymeric solution is incapable of dissolving the first polymeric solution.

According to some embodiments of the invention, the electrospun shell comprises a polymer selected from the group consisting of poly (e-caprolactone) (PCL), poly(ethylene glycol), polylactide, polyglycolide, poly(lactide-coglycolide), poly(ethylene oxide), poly(caprolactone), collagen, albumin, alginate, chitosan, starch, hyaluronic acid, and whereas the electrospun coat comprises a polymer selected from the group consisting of poly(ethylene glycol), polylactide polyglycolide, poly(lactide-coglycolide), poly(ethylene oxide), alginate, starch, hyaluronic acid.

According to some embodiments of the invention, a solvent of the first polymeric solution evaporates faster than a solvent of the second polymeric solution.

According to some embodiments of the invention, the electrospinning is effected using a rotating collector.

According to some embodiments of the invention, a solvent of the second polymeric solution is capable of evaporating through the internal surface of the shell.

According to some embodiments of the invention, the second polymeric solution is capable of wetting the internal surface of the shell.

According to some embodiments of the invention, a thickness of the shell is from about 100 nm to about 20 micrometer.

According to some embodiments of the invention, an internal diameter of the microtube is from about 50 nm to about 20 micrometer.

According to some embodiments of the invention, the first and the second polymeric solutions are selected from the group consisting of: 10% poly (e-caprolactone) (PCL) in chloroform ($CHCl_3$) and dimethylforamide (DMF) (80:20 by weight) as the first polymeric solution and 4% poly(ethylene oxide) (PEO) in water ($H_2O$) and ethanol (60:40 by weight) as the second polymeric solution, 10% PCL in $CHCl_3$ and DMF (80:20 by weight) as the first polymeric solution and 6% PEO in $H_2O$ and ethanol (60:40 by weight) as the second polymeric solution, 9% PCL in $CHCl_3$ and DMF (90:10 by weight) as the first polymeric solution and 7% PEO in $H_2O$ as the second polymeric solution, and 10% PCL in $CHCl_3$ and DMF (80:20 by weight) as the first polymeric solution and 9% poly(vinyl alcohol) (PVA) in water and ethanol (50:50 by weight) as the second polymeric solution.

According to some embodiments of the invention, the first polymeric solution comprises polyethylene glycol (PEG).

According to some embodiments of the invention, the shell comprises pores.

According to some embodiments of the invention, the first and the second polymeric solutions are biocompatible.

According to some embodiments of the invention, the microtube comprises a length of about 5-20 centimeters (cm).

According to some embodiments of the invention, the microtube comprises a plurality of microtubes.

According to some embodiments of the invention, the plurality of microtubes are attached to a coupling element.

According to some embodiments of the invention, the plurality of microtubes are connected to a reservoir which comprises the medicament or the diagnostic agent.

According to some embodiments of the invention, the plurality of microtubes are connected to a plurality of reservoirs.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A—Magnification is ×5000, size bar=5 μm; FIG. 1B—Magnification is ×1000, size bar=20 μm.

FIG. 3A depicts an exemplary embodiment of a device for delivering an active agent according to one embodiment of the invention. Device 10 includes microtube 14 attached to coupling element 12 via an opening tip of microtube 14 while allowing liquid flow through coupling element 12 into microtube 14.

FIG. 3B depicts an exemplary embodiment of a system for delivering an active agent according to one embodiment of the invention. System 100 is composed of microtube 14, while coupling element 12 is connected to tube 16 (e.g., a catheter, a cannula, a needle). Tube 16 can contact microtube 14 or be close to microtube 14 such that the liquid which flows within tube 16 can enter microtube 14 by diffusion and/or capillary rise.

DESCRIPTION OF SPECIFIC EMBODIMENTS OF THE INVENTION

The present invention, in some embodiments thereof, relates to methods and kits for delivering a medicament or a diagnostic agent to a subject and, more particularly, but not exclusively, to the use of electrospun microtubes for infusion of a medicament into a tissue-of-interest.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing some embodiments of the invention to practice, the present inventor has uncovered that electrospun microtubes can be used in the delivery of a medicament (e.g., a drug) and/or a diagnostic agent (e.g., an isotope) to a subject.

Figure 1A:
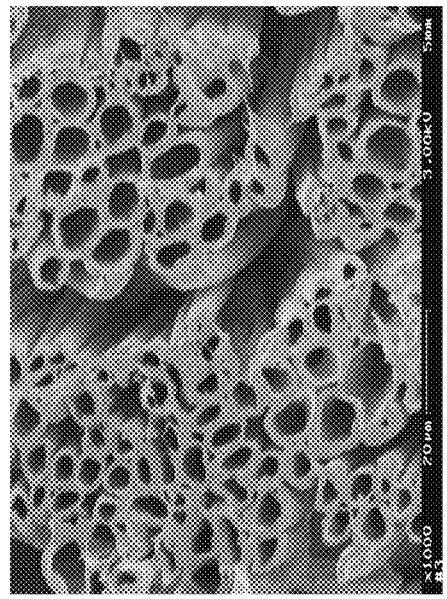
FIGS. 1A-B are scanning electron micrograph (SEM) depicting the microtubes comprised in the kit according to some embodiments of the invention. Shown are cross-sections through the capillary network formed by the electrospun microtubes. Microtubes were formed of PCL solution as a first polymeric solution (for the shell) and PEO solution as a second polymeric solution (for the coat over the internal surface of the shell).
Figure 1B:
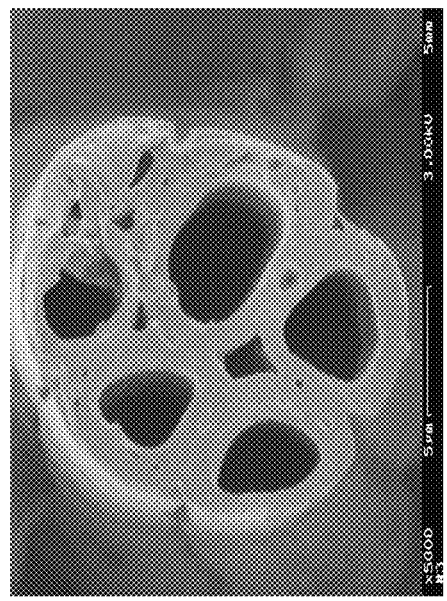
Figure 2:
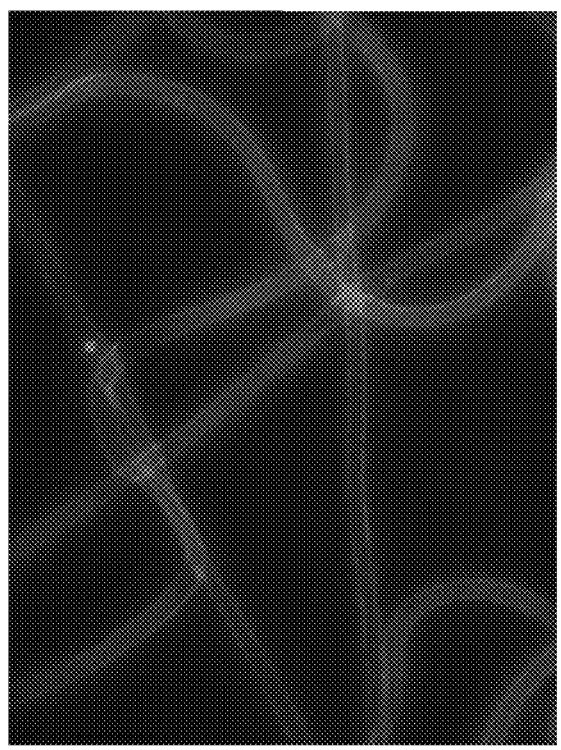
FIG. 2 is a fluorescence microscope image depicting diagnostic agent delivery according to some embodiments of the invention. Microtubes (with an electrospun shell and an electrospun coat over the internal surface of the shell) were filled (using a capillary rise) with an aqueous solution containing 2% Rhodamine. Note the presence of Rhodamine molecules (red signal) within the microtube network. The internal diameter of the microtubes (capillaries) is 5-15 micrometer (μm). Magnification is ×500.

Thus, as is shown in FIGS. 1a-b and 2 and described in Example 1 of the Examples section which follows, the present inventor produced electrospun microtubes which form a capillary network for delivering a labeled molecule therethrough. The capillaries inlets were coupled with a Teflon tube and a droplet of a solution containing the labeled molecule (Rhodamine) entered the microtube network by capillary rise. As shown in FIG. 2, following 8 minutes the Rhodamine molecules reached the end of the microtube (e.g., 5 cm). These results suggest the use of electrospun microtubes for targeted delivery of a medicament or a diagnostic agent to a subject.

According to one aspect of the invention, there is provided a method of delivering an active agent (a medicament or a diagnostic agent) to a subject in need thereof. The method comprising: (a) introducing a microtube configured to deliver the medicament or the diagnostic agent into the subject, the microtube comprises an electrospun shell and an electrospun coat over an internal surface of the shell; and (b) administering the medicament or the diagnostic agent through the microtube, thereby delivering the medicament or the diagnostic agent to the subject.

As used herein the phrase a "subject" refers to any animal subject e.g., a mammal, e.g., a human being.

As used herein the term "medicament" refers to a therapeutic agent capable of treating a pathology in subject in need thereof.

According to some embodiments of the invention, the medicament comprises a physiological fluid such as, a saline, blood or blood components, e.g., plasma, red blood cells, coagulation factors, white blood cells, platelets, leukocytes, neutrophils, and the like.

According to some embodiments of the invention the medicament comprises a drug or a combination of several drugs.

According to some embodiments of the invention, the drug comprises a biological moiety such as a polypeptide (e.g., a receptor agonist, an antagonist, a hormone, a growth factor, an antibody, an immunotoxin, an enzyme), a toxin, a DNA molecule (e.g., an antisense oligonucleotide, a DNAzyme, an expression vector encoding a gene-of-interest) an RNA molecule (e.g., a Ribozyme, an siRNA, an RNA antisense molecule) or a combination or conjugation thereof.

According to some embodiments of the invention, the drug is a small molecule, i.e., having a molecular weight which is less than 0.15 kDa.

According to some embodiments of the invention, the drug comprises a synthetic moiety such as anti cancer drugs. Following is a non-limiting list of anti cancer drugs which can be delivered by the microtube of the invention: Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to some embodiments of the invention, the medicament comprises a radiation seed particle for seed implantation or brachytherapy (using e.g., $I^{129}$ or $Pd^{103}$) [see e.g., Hypertext Transfer Protocol://World Wide Web (dot) oncura (dot) com]. Radiation seed particles may be used for a localized treatment of cancerous tumors (e.g., for prostate cancer).

According to some embodiments of the invention, the medicament comprises a vitamin (e.g., a naturally extracted or a synthetic vitamin).

According to some embodiments of the invention, the medicament comprises gas molecules (e.g., air, oxygen) saturated in a solution (e.g., an aqueous solution). For example, a medicament comprising gas molecules can be delivered to ischemic tissues (e.g., ischemic heart) to treat ischemia.

As used herein the term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to some embodiments of the invention, the medicament comprises a therapeutically effective amount of the therapeutic agent.

As used herein the phrase "therapeutically effective amount" means an amount of active ingredients (the therapeutic agent, e.g., the drug) effective to prevent, alleviate or ameliorate symptoms of a pathology or prolong the survival of the subject being treated.

As used herein the term "diagnostic agent" refers to a molecule which can be directly or indirectly detected and is used for diagnostic purposes. According to some embodiments of the invention, the diagnosis is effected in vivo (i.e., within a living subject) using e.g., MRI, CT, radiography and fluoroscopy. Non-limiting examples of diagnostic agents include small molecular contrast media (SMCM; e.g., less than 1 kDa) and large macromolecules contrast media (MMCM) such as Gd-DTPA, Gd-DTPA-BMA, Gd-DOTA, diatrizoate, Iohexol, Iopamidol Iodixano, Urografin (diatrizoate), Omnipaque (iohexol), Hexabrix (ioxaglate), Visipaque (iodixanol), Isovist (iotrolan), Ultravist (iopramide), Optiray (ioversol), radio-isotopes such as Technetium 99 m, iodine 123 ($^{123}$I), iodine 124 ($^{124}$I), TI-201, dual-isotope TI-201 and Tc-99m, thallium-201, F-18 FDG, dual isotope F-18 FDG and Tc-99m, indium-111, dual isotope thallium-201 and indium-111, Gallium-67, erbium-171 and samarium-153.

The therapeutic or diagnostic agent can be provided per se or may form part of a pharmaceutical composition where it is mixed with suitable carriers or excipients.

As used herein a "pharmaceutical composition" refers to a preparation of one or more of the therapeutic/diagnostic agents with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Any of the active agents described hereinabove (i.e., the medicament or the diagnostic agent) can be or form part of a suspension, solution, emulsion in oily or aqueous vehicles, dispersion, a melted agent and the like and may contain formulatory agents such as suspending, stabilizing and/or dispersing agents. According to some embodiments of the invention, the suspension or the solution is aqueous. Other formulations such as aerosols and the like are also contemplated.

Formulations for administering into the subject may be presented in unit dosage form, e.g., in ampoules or in multi-dose containers with optionally, an added preservative.

As used herein the term "microtube" refers to a hollow tube having an inner diameter from about 50 nm to about 50 µm and an outer diameter from about 0.5 µm to about 100 µm.

According to some embodiments of the invention the inner diameter of the microtube shell of the invention can vary from about 100 nm to about 20 µm, e.g., from about 200 nm to about 10 µm, e.g., from about 500 nm to about 5 µm, e.g., from about 1 µm to about 5 µm, e.g., about 3 µm.

According to some embodiments of the invention the thickness of the microtube shell of the invention can vary from a few nanometers to several micrometers, such as from about 100 nm to about 20 µm, e.g., from about 200 nm to about 10 µm, from about 100 nm to about 5 µm, from about 100 nm to about 1 µm, e.g., about 500 nm.

According to some embodiments of the invention, the microtube may have a length which is from about 0.1 millimeter (mm) to about 20 centimeter (cm), e.g., from about 1-20 cm, e.g., from about 5-10 cm.

The microtube is configured to deliver the active agent (i.e., the medicament and/or the diagnostic agent) into the subject, i.e., enables a flow and release of the active agent into the subject (e.g., an infusion microtube).

The microtube of the invention can be an individual microtube (e.g., single or separated) or can comprise a plurality of microtubes (e.g., an aligned array) which can be either connected to each other or separated (as single, not-connected microtubes).

As used herein the term "introducing" refers to implanting the microtube in the subject.

According to some embodiments of the invention, the microtube is introduced to a tissue-of-interest. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue and hematopoietic tissue.

The microtube of some embodiments of the invention may be implanted in a subject using methods which are well known in the art. For example, the microtube can be implanted subcutaneously, intradermally, or into any body tissue (e.g., cavity such as abdomen). In an exemplary embodiment the microtube is implanted in an affected tissue, e.g., tumor, as will be described in details below.

The microtube of some embodiments of the invention may be introduced using a catheter (e.g., by laparoscopy).

The microtube of some embodiments of the invention may be introduced by injection. For example, a microtube can be filled with the medicament or diagnostic agent and then cut to small fragments of microtubes (fragments of hollow fibers), each having a length of few a microns (e.g., 10-2000 µm). The small pieces of the microtube can be injected with a syringe connected to a long needle (e.g., a needle having a length of 5-30 cm) at the tissue-of-interest. Once injected, the active agent can be released from the microtube so as to achieve a therapeutic effect (e.g., for brachytherapy).

According to some embodiments of the invention, the microtube is implanted in a subject such that the tip of the microtube is implanted in or in close proximity to the tissue-of-interest. In certain embodiments the microtube is attached to a reservoir which comprises the active agent. In this case, one end of the microtube is attached to the reservoir (directly or indirectly as described hereinbelow), wherein the distal end of the microtube is at or in proximity to the tissue.

As used herein the term "proximity" refers to being in a cavity of the tissue, for example, if the tissue in which the active agent is released is a blood vessel (artery or vein) the cavity is a lumen of such a blood vessel, or if the tissue in which the active agent is released is a heart chamber, then the cavity is an atrium or a ventricle.

According to some embodiments of the invention, one end of the microtube is placed outside the body, or subcutaneously.

According to some embodiments of the invention, the delivery of the active agent from the microtube to the subject is performed via the microtube tips.

As used herein the term "administering" refers to providing or inserting the active agent through the microtube by injection, diffusion, capillary rise and/or forced flow of liquid comprising the medicament or the diagnostic agent.

According to some embodiments of the invention, administering by injection is performed using an extra thin needle capable of penetrating the microtube shell and/or entering the microtube lumen. The needle may have a diameter which is from 5-30 µm. A non-limiting example of a needle having a pointed end with a diameter of 20-30 microns is described in U.S. Pat. No. 5,100,432 to Matsutani Masaaki, and is incorporated herein by reference.

According to some embodiments of the invention, administering by diffusion or capillary rise is performed by contacting a liquid comprising the active agent with the microtube(s) tip. Contacting can be, for example, by placing a catheter or a cannula near the microtube(s) tip (see for example, FIG. 2 and Example 1 of the Examples section which follows). According to some embodiments of the invention, the catheter is placed on the skin or is implanted subcutaneously and runs through the implantation site where it comes in contact with the microtube, such as through a coupling element (e.g., adaptor).

According to some embodiments of the invention, administering by a forced flow of a liquid is performed using a pump which forces the liquid containing the active agent to flow into the microtube.

According to some embodiments of the invention, once the liquid flows through the microtubes tip, the liquid may flow within the microtube using a capillary force.

According to some embodiments of the invention, administering the active agent through the microtube [step (b)] is performed prior to introducing the microtube into the subject [step (a)]. For example, a microtube can be filled with a liquid comprising the active agent and then be implanted into the subject.

According to some embodiments of the invention, introducing the microtube into the subject [step (a)] is performed prior to administering of the active agent through the microtube [step (b)].

According to some embodiments of the invention, following a pre-determined time the microtube can be removed from the subject. For example, when treating a cancerous tumor with a microtube which delivers a toxin or a radiation seed (e.g., for brachytherapy), the microtube can be removed from the subject after a therapeutic effect at the tissue-of-interest is achieved (e.g., to prevent a non-specific effect on the surrounding healthy cells).

The microtube(s) described hereinabove can be included in a device for drug or diagnostic agent delivery.

In one embodiment of the present invention, the microtube is attached directly or indirectly to a coupling element. FIG. 3a depicts a specific configuration of such a device. Device 10 includes microtube 14 attached to coupling element 12 while allowing fluid communication.

Coupling element 12 is an element which connects (holds together) one physical element to another. The coupling element is typically used to allow directed fluid communication. Thus, coupling element 12 adapts microtube(s) 14 to an additional microtube(s) 14, or other tubes (e.g., a catheter, a needle, a syringe), a reservoir, a filter and/or a tissue (e.g., anastomosis element for attaching to a tissue, e.g., intestine). Coupling element 12 can be of a tubular structure (e.g., a tube) with an inlet and an outlet having a similar diameter. Additionally or alternatively, coupling element 12 may have a conical shape in which the inlet is narrower than the outlet. It may be rigid or flexible (e.g., a Teflon tape) depending on the intended use. Coupling element 12 can be configured to control the rate of flow.

A non-limiting example of coupling element 12 is a Teflon tube (can be purchased from SCI Scientific Commodities Inc. Lake Havasu City, Ariz.).

Attachment of coupling element 12 to microtube(s) 14 can be performed using an adhesive (a glue). Non-limiting examples of adhesives which can be used to attach microtube 14 to coupling element 12 include, Sulfacrylate (AZoM, Warriewood NSW, Australia), an alpha cyanoacrylate glue which includes various esters of acrylic acid and its derivatives and does not provoke allergy or stimulate tumorogenesis; an adhesive such as the Bipax epoxy resin glue (Tra-Con, Inc., Medford, Mass.; see e.g., Yoneda, M. et al., 2005, Hypertension, 46: 58-65) and a cyanoacrylate glue (Pattex N27, Henkel adhesives, Duesseldorf, Germany).

Additionally or alternatively, attachment of coupling element 12 to microtube(s) 14 can be performed by melting (e.g., by heat in a controllable way) the edges of coupling element 12 and microtube 14.

In another embodiment, coupling element 12 is attached to a tube (e.g., a cannula or a catheter) typically of larger diameter than that of the microtube of the present invention. Such a configuration is depicted in FIG. 3b whereby system 100 is composed of microtube 14, while coupling element 12 is connected to tube 16 (e.g., a catheter, a cannula, a needle). Tube 16 can contact microtube 14 or be close to microtube 14 so as to enable fluid communication between tube 16 and microtube 14, e.g., by diffusion and/or capillary rise.

Figure 4A:
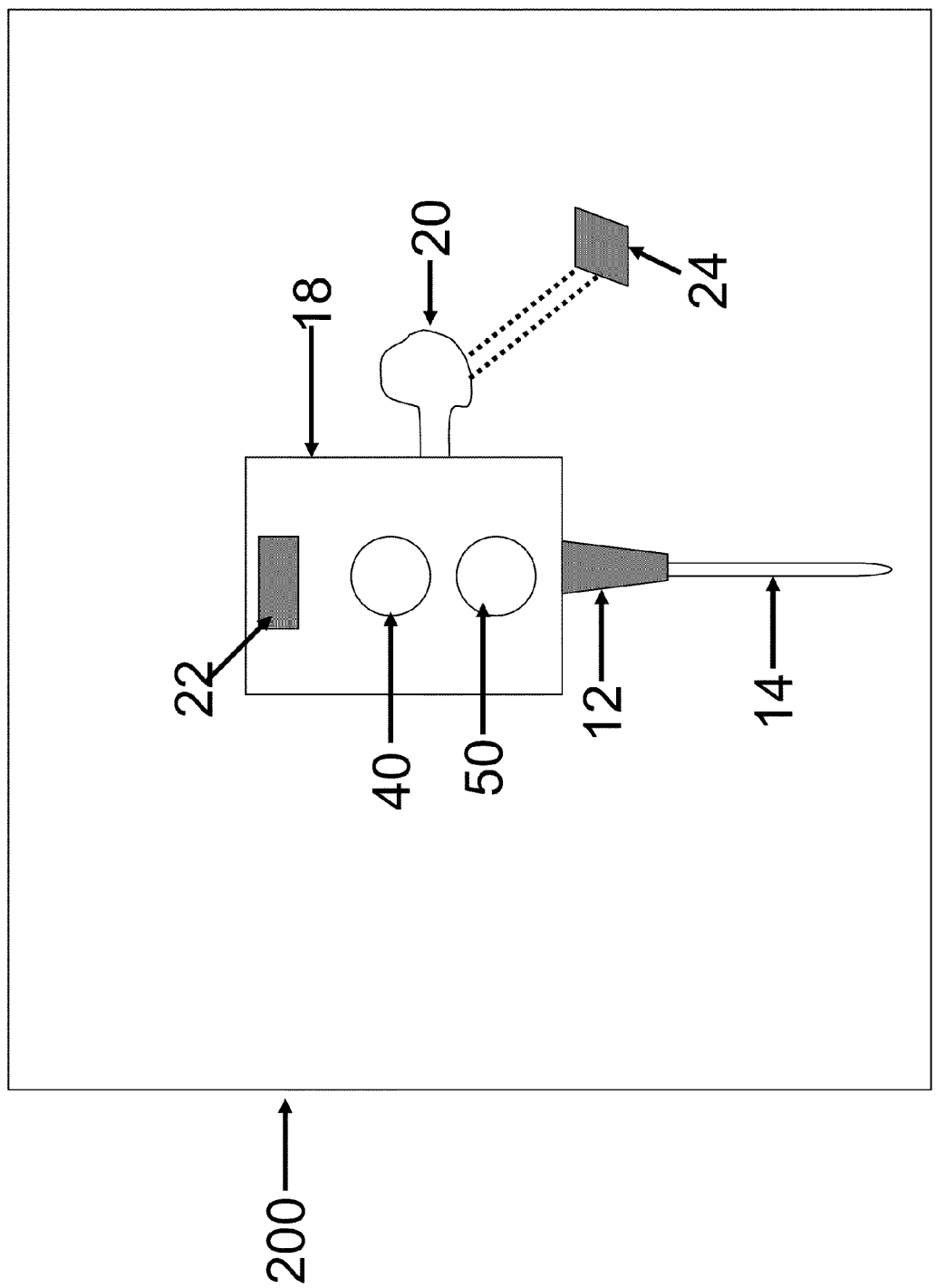
FIG. 4A depicts an exemplary embodiment of a system for delivering an active agent according to one embodiment of the invention. System 200 comprises reservoir 18 being in fluid communication with microtube 14. Attachment of microtube 14 to reservoir 18 is through coupling element 12 when fluid communication is maintained. Reservoir 18 may include seal 22 formed of a puncturable material. Pump 20 may include an electrically controlled valve 24 (operated by a power source) which is associated with pump 20 to dispense medicament 40 or diagnostic agent 50 from reservoir 18.

In another embodiment the microtube is attached to a reservoir which comprises the active agent. A specific embodiment of such a system is described in FIG. 4a. Thus, system 200 comprises reservoir 18 being in fluid communication with microtube 14. Reservoir 18 contains medicament 40 or diagnostic agent 50. Attachment of microtube 14 to reservoir 18 is through coupling element 12 and fluid communication is maintained.

Reservoir 18 is replenished through seal 22 such as by injecting in medicament 40 or diagnostic agent 50. Seal 22 is typically formed of a puncturable material (i.e., a material which can be punctured) which can reseal when a needle is withdrawn.

Reservoir 18 may be an implantable reservoir (e.g., which is implanted subcutaneously or at or in proximity to a tissue-of-interest, such as a tumor or an affected gland) or an external reservoir (e.g., which is attached on the skin from the outer side of the subject's body). The release of medicament 40 or diagnostic agent 50 from reservoir 18 can be controlled by remote operation.

According to some embodiments of the invention, the volume of the active agent which can be contained in implantable reservoir 18 is from a range of about 1-200 milliliter (ml), e.g., about 1-100 ml, e.g., about 2-100 ml, e.g., about 5-50 ml. According to some embodiments of the invention, replenishment of implantable reservoir 18 with the active agent (medicament 40 or diagnostic agent 50) is performed through a penetrable septum which may be located directly under the subject's skin.

According to some embodiments of the invention, reservoir 18 is connected to pump 20 which releases the active agent from reservoir 18 to microtube(s) 14. Pump 20 can be a peristaltic pump, an electrical or a mechanical pump.

According to some embodiments of the invention, pump 20 may include electrically controlled valve 24 (operated by a power source) which is associated with pump 20 to dispense medicament 40 or diagnostic agent 50 from reservoir 18. As used herein the phrase "associated with a pump" refers to either a direct or an indirect contact between electrically controlled valve 24 and pump 20. For example, an indirect contact may be via any signaling route (e.g., radio frequency).

Figure 4B:
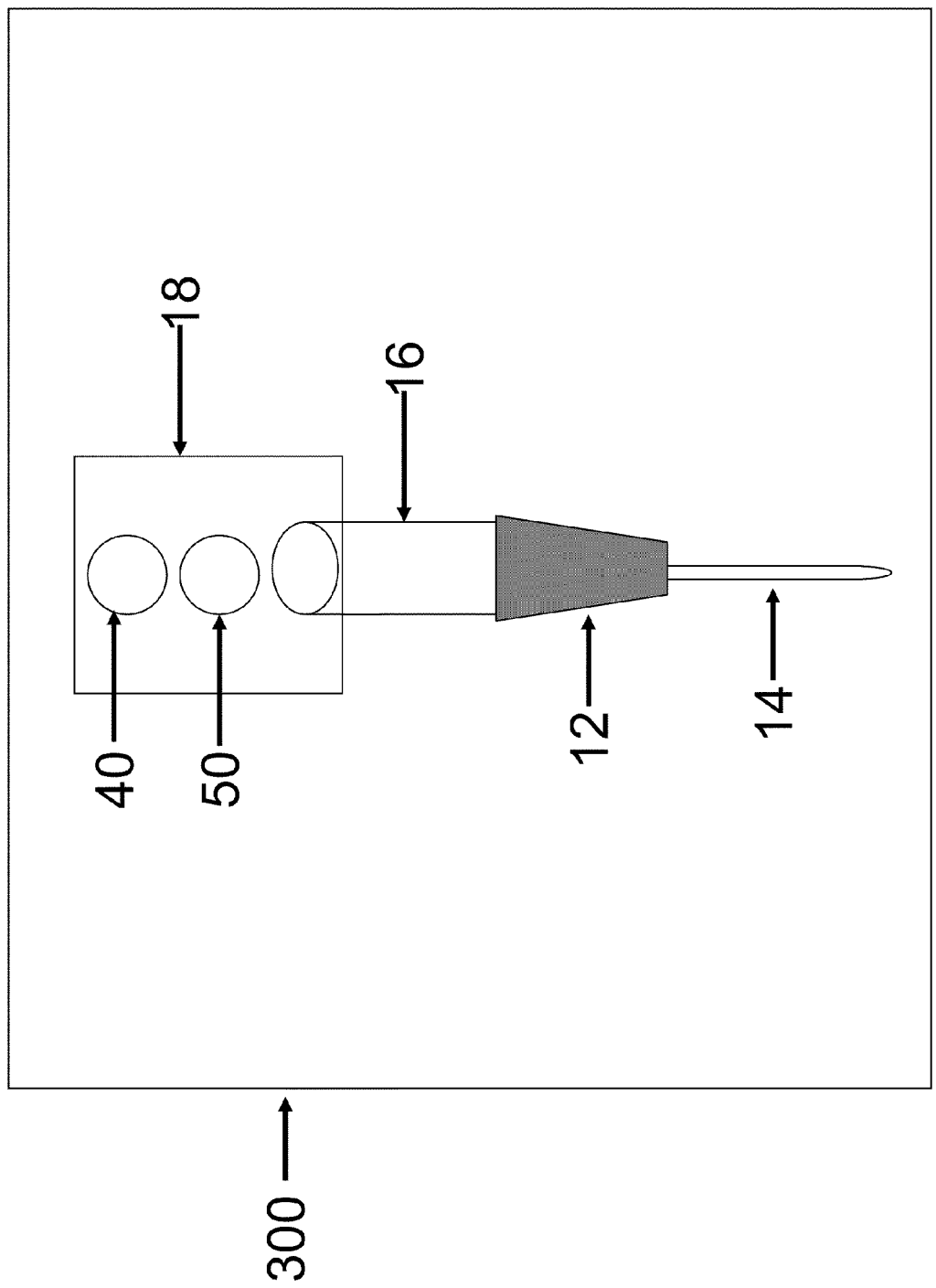
FIG. 4B depicts an exemplary embodiment of a system for delivering an active agent according to one embodiment of the invention. System 300 comprises drug reservoir 18 containing active agent 40 or 50. Drug reservoir 18 is in fluid communication with tube 16. Tube 16 is also in fluid communication with coupling element 12, which is connected to microtube 14, while maintaining fluid communication.
Figure 4C:
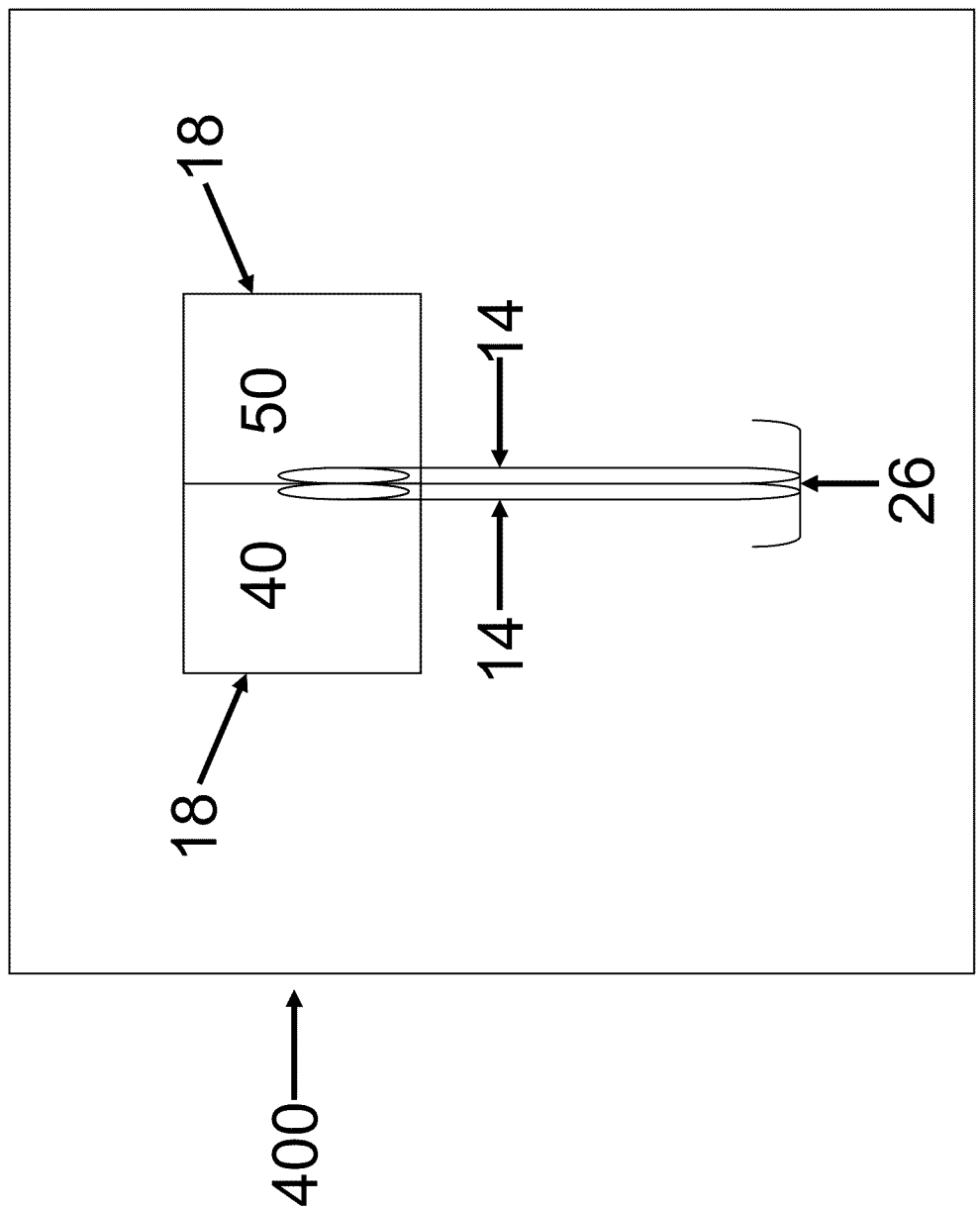
FIG. 4C depicts an exemplary embodiment of a system for delivering an active agent according to one embodiment of the invention. System 400 having a plurality of reservoirs 18 each comprising distinctive active agent 40 or 50 while being in fluid communication with microtube 14 of microtube network 26.

In another embodiment, the microtube is attached to a coupling element which is connected to a tube (e.g., a cannula or a catheter). The tube is further connected on its other end to a reservoir containing the active agent. In this embodiment the reservoir may be either a non-implantable reservoir (in which case the tube is implantable and runs across the implantation site in the skin) or an implantable reservoir. A specific embodiment of such a system is described in FIG. 4b. Thus, system 300 comprises drug reservoir 18 containing medicament 40 and/or diagnostic agent 50 being in fluid communication with tube 16. Tube 16 is also in fluid communication with coupling element 12, which is connected (while maintaining fluid communication) to microtube 14.

A plurality of reservoirs (i.e., at least two reservoirs) each, for example, containing a different active agent (or different concentrations of the active agent), can be attached to a microtube network. Such a configuration is depicted in FIG.

4c which shows system 400 having a plurality of reservoirs 18 each being in fluid communication with microtube network 26, which includes microtubes 14. According to some embodiments of the invention, each of the plurality of reservoirs 18 is connected to a single microtube 14 of microtube network 26.

According to some embodiments of the invention, prior to delivering the active agent to the subject (i.e., to the cells or tissue of the subject), the liquid comprising the active agent is filtered. The filter is used to ensure removal of unwanted debris from the liquid comprising the active agent. The filter(s) may be placed within reservoir 18, tube 16, coupling element 12 and/or infusion microtube(s) 14. The pore size of the filter(s) are selected to prevent passage of unwanted debris and yet to enable flow of the active agent to the cell/tissue of the subject. The filter(s) may be replaced occasionally, depending on the accumulation of debris thereon.

According to some embodiments of the invention, any of the elements described hereinabove, e.g., microtube(s) 14, coupling element 12, the adhesives, tube (catheter, cannula) 16, reservoir 18 and the filter(s) is a biocompatible element (i.e., an element made of a biocompatible material, which when in contact with cells, tissues or body fluid of an organism does not induce adverse effects such as immunological reactions and/or rejections, cellular death and the like). A biocompatible element can be also biodegradable [i.e., an element/material which can be degraded (broken down) in the physiological environment such as by proteases or other enzymes produced by living organisms such as bacteria, fungi, plants and animals]. Biodegradability of materials (e.g., polymers) depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients.

The elements described herein can be included in a diagnostic or therapeutic kits, such as an FDA approved kit, which may contain one or more unit dosage forms containing the active ingredients. The pack may, for example, comprise metal or plastic foil, such as a blister pack. The pack or dispenser device may be accompanied by instructions for administering and use. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein, the phrase "electrospun shell" refers to a hollow element of a tubular shape, made of one or more polymers, produced by the process of electrospinning as detailed hereinbelow.

According to some embodiments of the invention, electrospun shell may comprise pores.

As used herein the phrase "electrospun coat" refers to a thin layer covering the internal surface of the shell of the microtube of the invention which is made of one or more polymers by the process of electrospinning as detailed hereinbelow.

One of ordinary skill in the art will know how to distinguish an electrospun object from objects made by means which do not comprise electrospinning by the high orientation of the macromolecules, the skin (e.g., shell) morphology, and the typical dimensions of the microtube which are unique to electrospinning.

According to some embodiments of the invention, the microtube is produced by co-electrospinning of two polymeric solutions through co-axial capillaries, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution.

As used herein the phrase "co-electrospinning" refers to a process in which at least two polymeric solutions are electrospun from co-axial capillaries (i.e., at least two capillary dispensers wherein one capillary is placed within the other capillary while sharing a co-axial orientation) forming the spinneret within an electrostatic field in a direction of a collector. The capillary can be, for example, a syringe with a metal needle or a bath provided with one or more capillary apertures from which the polymeric solution can be extruded, e.g., under the action of hydrostatic pressure, mechanical pressure, air pressure and high voltage.

The collector serves for collecting the electrospun element (e.g., the electrospun microtube) thereupon. Such a collector can be a rotating collector or a static (non rotating) collector. When a rotating collector is used, such a collector may have a cylindrical shape (e.g., a drum), however, the rotating collector can be also of a planar geometry (e.g., an horizontal disk). The spinneret is typically connected to a source of high voltage, such as of positive polarity, while the collector is grounded, thus forming an electrostatic field between the dispensing capillary (dispenser) and the collector. Alternatively, the spinneret can be grounded while the collector is connected to a source of high voltage, such as with negative polarity. As will be appreciated by one ordinarily skilled in the art, any of the above configurations establishes motion of positively charged jet from the spinneret to the collector. Reverse polarity for establishing motions of a negatively charged jet from the spinneret to the collector are also contemplated.

For electrospinning, the first polymeric solution is injected into the outer capillary of the co-axial capillaries while the second polymeric solution is injected into the inner capillary of the co-axial capillaries. In order to form a microtube (i.e., a hollow structure, as mentioned above), the first polymeric solution (which is for forming a shell of the microtube) solidifies faster than the second polymeric solution (also referred herein as a core polymeric solution, and is for forming a coat over an internal surface of the shell). In addition, the formation of a microtube also requires that the solvent of the second polymeric solution is incapable of dissolving the first polymeric solution.

The solidification rates of the first and second polymeric solutions are critical for forming the microtube. For example, for a microtube of about 100 µm, the solidification of the first polymer (of the first polymeric solution) can be within about 30 milliseconds (ms) while the solidification of the second polymer (of the second polymeric solution) can be within about 10-20 seconds. The solidification may be a result of polymerization rate and/or evaporation rate.

According to some embodiments of the invention, the solvent of the first polymeric solution evaporates faster than the solvent of second polymeric solution (e.g., the solvent of the first polymeric solution exhibits a higher vapor pressure than the solvent of the second polymeric solution).

According to some embodiments of the invention, the rate of evaporation of the solvent of the first polymeric solution is at least about 10 times faster than that of the solvent of the second polymeric solution. The evaporation rate of the solvent of the first polymeric solution can be at least about 100 times faster or at least about 1000 times faster than the evaporation rate of the solvent of second polymeric solution. For example, the evaporation of chloroform is significantly faster than the evaporation of an aqueous solution (water) due to the high vapor pressure at room temperature of the chloroform (195 mmHg) vs. that of the aqueous solution (23.8 mmHg).

When selecting a solvent of the second polymeric solution which is incapable of dissolving the first polymeric solution (i.e., a non-solvent of the first polymeric solution), the polymer of the first polymeric solution can solidify (e.g., through precipitation) and form a strong microtube shell which does not collapse, and which is characterized by an even thickness. According to some embodiments of the invention, the first polymeric solution (e.g., the solvent of the first polymer) is substantially immiscible in the solvent of the second polymeric solution.

The solvent of the second polymeric solution may evaporate while the polymer (of the second polymeric solution) forms a thin layer on the internal surface of the shell.

According to some embodiments of the invention, the solvent of the second polymeric solution is capable of evaporating through the internal surface of the shell.

The flow rates of the first and second polymeric solutions can determine the microtube outer and inner diameter and thickness of shell. Non-limiting examples are shown in Table 1 hereinbelow.

naturally occurring biomaterials. Examples include, but are not limited to, aliphatic polyesters, poly(amino acids), copoly (ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use by the invention can also include biosynthetic polymers based on sequences found in naturally occurring proteins such as those of collagen, elastin, thrombin, fibronectin, or derivatives thereof or, starches, poly(amino acids), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, albumin, fibrinogen, and alginate.

As used herein, the phrase "co-polymer" refers to a polymer of at least two chemically distinct monomers. Non-limiting examples of co-polymers include, polylactic acid (PLA)-polyethyleneglycol (PEG), polyethylene glycol terephthalate (PEGT)/polybutylene terephthalate (PBT), PLA-polyglycolic acid (PGA), PEG-polycaprolactone (PCL) and PCL-PLA.

As used herein, the phrase "blends of polymers" refers to the result of mixing two or more polymers together to create a new material with different physical properties.

According to some embodiments of the invention, the polymers of the first and the second polymeric solutions are biocompatible.

TABLE 1

Effect of the flow rates of the two polymeric solutions during electrospinning on microtube diameter and thickness of shell

| System No. | System: First polymeric solution/Second polymeric solution | Flow rates (ml/hr) | R Outer Fiber radius (μm) | d Shell thickness (μm) | V Voltage (kV) | Electrostatic field kV/cm |
|---|---|---|---|---|---|---|
| M5 | First polymeric solution | 4 | 3.0-4.5 | 0.5 ± 0.1 | 8.5 | 0.43 |
|  | Second polymeric solution | 0.5 |  |  |  |  |
| M10 | First polymeric solution | 10 | 2.3-4.0 | 1.0 ± 0.1 | 8 | 0.5 |
|  | Second polymeric solution | 0.3 |  |  |  |  |
| M11 | First polymeric solution | 10 | 3-6 | 1.0 ± 0.1 | 9 | 0.56 |
|  | Second polymeric solution | 2 |  |  |  |  |

Table 1: Electrospinning was performed with the following solutions: First polymeric solution (for forming the shell) was 10% PCL in CHCl$_3$/DMF (8:2 weight/weight); second polymeric solution (for forming the coat) was 4% PEO in H$_2$O/EtOH (6:4, weight/weight). PCL 80K; PEO 600K. The temperature during electrospinning was of 22-26° C. The relative humidity was 58%, 52% and 53% for systems M5, M10 and M11, respectively. The flow rates were measured in milliliter per hour (ml/hr); the outer microtube radius and the shell thickness were measured in microns (μm). The voltage (V) was measured kilo volt (kV) and the electrostatic field in kV per centimeter (kV/cm). The resulting tubes were hollow (good tubes in systems M5 and M11, and mostly good in system M10).

As used herein the phrase "polymeric solution" refers to a soluble polymer, i.e., a liquid medium containing one or more polymers, co-polymers or blends of polymers dissolved in a solvent. The polymer used by the invention can be a natural or a synthetic biocompatible and/or biodegradable polymer.

The phrase "synthetic polymer" refers to polymers that are not found in nature, even if the polymers are made from Non-limiting examples of biocompatible polymers include polyesters (PE), PCL, Calcium sulfate, PLA, PGA, PEG, polyvinyl alcohol, polyvinyl pyrrolidone, Polytetrafluoroethylene (PTFE, teflon), polypropylene (PP), polyvinylchloride (PVC), Polymethylmethacrylate (PMMA), polyamides, segmented polyurethane, polycarbonate-urethane and thermoplastic polyether urethane, silicone-polyether-urethane, silicone-polycarbonate-urethane collagen, PEG-DMA, alginate, hydroxyapatite and chitosan, blends and copolymers thereof.

Examples of biodegradable polymers/materials include, but are not limited to, collagen (e.g., Collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), collagen, PEG-DMA, alginate, chitosan copolymers or mixtures thereof.

According to some embodiments, the polymeric solution can be made of one or more polymers, each can be a polymer or a co-polymer such as described hereinabove.

During the formation of the microtube shell (e.g., following the solidification of the first polymeric solution) the second polymeric solution flows within the internal surface of the shell.

According to some embodiments of the invention, the second polymeric solution is selected capable of wetting the internal surface of the shell.

Various polymeric solutions are capable of wetting other polymeric surfaces (for forming the shell). Following is a non-limiting list of pairs of polymeric solutions in which the second polymeric solution is capable of wetting the internal surface of the shell formed by the first polymeric solution.

TABLE 2

Pairs of polymeric solutions for producing the microtube of the invention

| First polymeric solution forming the shell | Second polymeric solution capable of wetting the internal surface of the shell |
|---|---|
| 10% poly (e-caprolactone) (PCL); in chloroform (CHCl$_3$) and dimethylforamide (DMF) (80:20 by weight) | 4% poly(ethylene oxide) (PEO); in water (H$_2$O) and ethanol (60:40 by weight) |
| Nylon 6,6 in formic acid 7 to 12 wt % | 4% poly(ethylene oxide) (PEO); in water (H$_2$O) and ethanol (60:40 by weight) |
| Poly(L-lactide-co-glycolide) (PLGA 10:90) in hexafluroisopropanol (HFIP) concentrations ranging from 2 to 7 weight % solution. | 4% poly(ethylene oxide) (PEO) in water (H$_2$O) and ethanol (60:40 by weight) |
| Poly(L-lactide-co-glycolide) (PLGA 15:85) hexafluroisopropanol (HFIP) concentrations ranging from 2 to 7 weight % solution. | 4% poly(ethylene oxide) (PEO); in water (H$_2$O) and ethanol (60:40 by weight) |
| poly(lactide-co-glycolide) (PLGA; l-lactide/glycolide_50/50) 1,1,1,3,3,3-hexafluoro-2-propanol (HFIP) concentrations ranging from 2 to 7 weight % solution. | 4% poly(ethylene oxide) (PEO); in water (H$_2$O) and ethanol (60:40 by weight) |
| polyglycolide (PGA) in chloroform 3-10 weight % solution. | 9% poly(vinyl alcohol) (PVA); in water and ethanol (50:50 by weight) |
| poly(L-lactide) (PLA) in chloroform 3-10 weight % solution. | 9% poly(vinyl alcohol) (PVA); in water and ethanol (50:50 by weight) |
| Segmented polyurethane in DMF and THF (80:20 by weight) | 9% poly(vinyl alcohol) (PVA); in water and ethanol (50:50 by weight) |
| Polyurethane in DMF and tetrahydrofuran, THF (80:20 by weight) | 9% poly(vinyl alcohol) (PVA); in water and ethanol (50:50 by weight) |
| PLGA (poly lactic-co-glycolic acid); in chloroform and DMSO (dimethyl sulfoxide) in chloroform and DMSO (80:20 by weight). | 9% poly(vinyl alcohol) (PVA); in water and ethanol (50:50 by weight) |
| 10% PCL in CHCl$_3$/DMF (80:20 by weight) | 6% PEO in H$_2$O/EtOH (60:40 by weight) |
| 9% PCL in CHCl$_3$/DMSO (90:10 by weight) | 7% PEO in H$_2$O |
| 10% PCL in CHCl$_3$/DMF (80:20 by weight) | 9% PVA in ethanol/water (50:50 by weight) |
| 10% PCL 80K CHCl$_3$:DMF (90:10 by weight) | 4% (w/w) PEO 600K; in ethanol:H$_2$O (26:74 by weight) |
| 10% PCL 80K + 1% PEG 6K CHCl$_3$:DMF (90:10 by weight) | 4% (w/w) PEO 600K; in ethanol:H$_2$O (26:74 by weight) |

The polymers forming the solutions and the solvents are provided by weight ratios, i.e., a weight/weight (w/w) ratio.

According to some embodiments of the invention, the polymeric solution is a mixture of at least one biocompatible polymer and a co-polymer (either biodegradable or non-biodegradable).

According to some embodiments of the invention, the first polymeric solution for forming the shell can be made of a polymer such as poly (ε-caprolactone) (PCL), poly(ethylene glycol), polylactide, polyglycolide, poly(lactide-coglycolide), poly(ethylene oxide), poly(caprolactone), collagen, albumin, alginate, chitosan, starch, hyaluronic acid, and blends and copolymers thereof.

According to some embodiments of the invention, the second polymeric solution for forming the coat over the internal surface of the shell can be made of a polymer such as poly (ethylene glycol), polylactide polyglycolide, poly(lactide-coglycolide), poly(ethylene oxide), alginate, starch, hyaluronic acid, and blends and copolymers thereof.

According to some embodiments of the invention, the first and the second polymeric solutions are selected from the group consisting of: 10% poly (e-caprolactone) (PCL) in chloroform (CHCl$_3$) and dimethylforamide (DMF) (80:20 by weight) as the first polymeric solution and 4% poly(ethylene oxide) (PEO) in water (H$_2$O) and ethanol (60:40 by weight) as the second polymeric solution, 10% PCL in CHCl$_3$ and DMF (80:20 by weight) as the first polymeric solution and 6% PEO in H$_2$O and ethanol (60:40 by weight) as the second polymeric solution, 9% PCL in CHCl$_3$ and DMF (90:10 by weight) as the first polymeric solution and 7% PEO in H$_2$O as the second polymeric solution, 10% PCL in CHCl$_3$ and DMF (80:20 by weight) as the first polymeric solution and 9% poly(vinyl alcohol) (PVA) in water and ethanol (50:50 by weight) as the second polymeric solution and 10% PCL in CHCl$_3$ and DMF (90:10 by weight) as the first polymeric solution and 4% (w/w) PEO in ethanol:H$_2$O (26:74 by weight) as a second polymeric solution.

To enable a flow of a liquid comprising the medicament or the diagnostic agent within the microtube, i.e., along the coat polymer covering the internal surface of the shell (which originates from the second polymer solution), the surface (thin film) formed by the coat polymer should be designed such that it can be wetted by the liquid. The ability to wet (wettability) polymer films by liquids is known in the art. For example, silicone oil or water can wet a surface made of a PEO polymer. The wettability of the coat polymer covering the internal surface of the shell can be controlled (e.g., improved) for example by attaching (e.g., using plasma treatment) functional groups such as hydroxyl group (OH) which increase the hydrophilicity of the coat [see Thurston R M, Clay J D, Schulte M D, Effect of atmospheric plasma treatment on polymer surface energy and adhesion, Journal of Plastic Film & Sheeting 23 (1): 63-78 Jan. 2007; which is incorporated within by reference].

As mentioned, the microtube shell may comprise pores (a "breathing" tube). Methods of forming "breathing" microtube (i.e., microtubes with pores in the shell thereof) are described in PCT/IB2007/054001 to Zussman E., et al., which is fully incorporated herein by reference. Briefly, "breathing" tubes can be formed by the inclusion of a high percent (e.g., at least 80%) of a volatile component such as tetrahydrofuran (THF), chloroform, acetone, or trifluoroethanol (TFE) in the first polymeric solution forming the shell, and/or by the inclusion of a water-soluble polymer such as polyethylene glycol (PEG) in the first polymeric solution forming the shell so that the first polymeric solution comprises a blend of polymers in which one is water-soluble and the other is water-insoluble (e.g., a blend of PEG and PCL). Alternatively, "breathing" microtubes can be formed by inducing pores in the shell after the completion of the electrospinning process, essentially as described in PCT WO 2006/106506 to the present inventor, which is fully incorporated herein by reference, such as by passing an electrical spark or a heated puncturing element through the electrospun shell, or by using a pulsed or continuous laser beam through the electrospun shell.

According to some embodiments of the invention, the first polymeric solution comprises PEG for inducing pores in the shell. For example, to generate pores greater (>) than 150 nm in diameter, the first polymeric solution may include about 4% PEG Mw 35 kDa. Similarly, to generate pores smaller (<) 150 nm in diameter, the first polymeric solution may include about 2% PEG MW 6 kDa.

As mentioned, delivery of the medicament or the diagnostic agent can be performed via the pores in the microtube shell.

According to some embodiments of the invention, the microtube shell is designed for selective passage of a certain medicament or diagnostic agents. The passage through the shell pores depends on the size and/or the electrical charge of the medicament or diagnostic agent with respect to the geometry (length and radius), surface energy, electrical charge of the shell pores, and the viscosity and surface tension of the liquid comprising the medicament or diagnostic agent.

According to some embodiments of the invention, the porosity [i.e., the ratio of the volume of the shell pores to the volume of the shell mass] and pore size can control the release of the medicament or diagnostic agent from the microtube. Increased porosity can result in a higher rate of release through the shell pores.

According to some embodiments of the invention, the microtube is designed such that the electrospun shell is semi-permeable (i.e., prevents passage of the medicament or diagnostic agent but enables the penetration of water or a physiological solution therethrough). Such a microtube can be substantially devoid of pores, or with pores having a diameter which is smaller than the medicament or diagnostic agent, or which exhibit a geometry which prevents passage of medicaments or diagnostic agents therethrough.

As mentioned, delivery of the medicament or the diagnostic agent can be performed via the microtube's opening.

According to some embodiments of the invention, at least one end of the microtube (e.g., the distal end which is in proximity to the tissue-of-interest) is subject to treatment with a supercritical fluid (e.g., liquid nitrogen) for e.g., 1-10 minutes, which freezes the microtube and preserves its openness. The frozen microtube can be further cut close to its end (using e.g., a razor blade).

According to some embodiments of the invention, the microtube end(s) can be cross-linked using e.g., glutaraldehyde (e.g., a solution of 10% v/v glutaraldehyde). Cross-linking can be performed on frozen (e.g., following treating with liquid nitrogen) or on as spun microtubes. Prior to use (e.g., prior to implantation into a subject), microtubes which were treated with a cross-linking agent such as glutaraldehyde are thoroughly washed with water or a physiological solution (e.g., saline).

As mentioned, the infusion microtube of the invention can be an individual microtube or form part of a plurality of microtubes. For the production of a single microtube a fork like clip is attached to the edge of the rotating disk. The disk is rotated for 1-2 seconds and individual microtubes are formed between the sides of the clip. In a similar way individual electrospun fibers were collected (see E. Zussman, M. Burman, A. L. Yarin, R. Khalfin, Y. Cohen, "Tensile Deformation of Electrospun Nylon 6,6 Nanofibers," *Journal of Polymer Science Part B: Polymer Physics*, 44, 1482-1489, 2006, herein incorporated by reference in its entirety).

Alternatively, when using a rotating collector, a plurality of microtubes can be formed and collected on the edge of the collector as described elsewhere for electrospun fibers (A. Theron, E. Zussman, A. L. Yarin, "Electrostatic field-assisted alignment of electrospun nanofibers", *Nanotechnology J.*, 12, 3: 384-390, 2001; herein incorporated by reference in its entirety).

The plurality of microtubes can be arranged on a single layer, or alternatively, the plurality of microtubes define a plurality of layers hence form a three dimensional structure. The microtubes can have a general random orientation, or a preferred orientation, as desired. For example, when the fibers are collected on a cylindrical collector such as a drum, the microtubes can be aligned predominantly axially or predominantly circumferentially. Different layers of the electrospun microtubes can have different orientation characteristics. For example, without limiting the scope of the present invention to any specific ordering or number of layers, the microtubes of a first layer can have a first predominant orientation, the microtubes of a second layer can have a second predominant orientation, and the microtubes of third layer can have general random orientation.

The microtube of the invention can be available as a dry fibrous mat(s) (e.g., as spun dry microtubes) or as a wetted mat(s) (e.g., following immersing or filling the microtube with a liquid).

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); D. H. Reneker, A. Yarn, E. Zussman, S. Koombhongse, and W. Kataphinan, "Nanofiber Manufacturing: Toward Better Process Control", in: Polymeric Nanofibers, ACS Symposium Series, Vol. 918, Ed. Reneker, D. H.; Fong, H., ACS, Washington D.C., 2005; A. L. Yarin, E. Zussman, A. Greiner, J. H. Wendorff, "Material encapsulation and transport in core-shell micro/nanofibers, polymer and carbon nanotubes and micro/nano channels", J. of Materials Chemistry, 17, 2585-2599, 2007; A. Greiner, J. H. Wendorff, A. L. Yarn, E. Zussman, "Biohybrid nanosystems with polymer nanofibers and nanotubes," Applied Microbiology and Biotechnology, 71, 387-393, 2006; D. H. Reneker, A. L. Yarn, E. Zussman, H. Xu, "Electrospinning of nanofibers from polymer solutions," Advances in Applied Mechanics (Review Paper), 41, 43-195, 2007; Z. M. Huang, Y. Z. Zhang, M. Kotaki, S. Ramakrishna (2003) Composites Science and Technology 63:2223; S. Ramakrishna, K. Fujihara, W.-e. Teo, Lim, T. C., Z. Ma, An Introduction to Electrospinning and Nanofibers, World Scientific Publishing Company, 2005; all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Polymer solutions and characterization—The polymers, poly (ε-caprolactone) (PCL) $M_n$ 80 kDa, poly(ethylene oxide) (PEO) $M_w$ 600 kDa, poly(vinyl alcohol) (PVA) $M_w$ 100 kDa and polyethylene glycol (PEG) Mn 6 kDa were purchased from Sigma-Aldrich and used without further treatment or purification. The solvents, chloroform, dimethylforamide (DMF), ethanol and the phosphate buffer saline (PBS-Dulbecco's) were also purchased from Sigma-Aldrich.

Deionized water was used for the aqueous solution. The compositions of the core and shell polymeric solutions are given in Table 3, hereinbelow.

TABLE 3

First and second polymeric solutions used for forming the shell and coat over internal surface of shell, respectively, of the microtubes used for target delivery of a medicament/diagnostic agent

| System No. | Polymeric Solution | Polymer | Conductivity (mS cm$^{-1}$) | Shear Viscosity (cP) |
|---|---|---|---|---|
| 1 | First | 10% PCL in CHCl$_3$/DMF 8:2 | 1 | 1300 |
|  | Second | 4% PEO in H$_2$O/EtOH 6:4 | 11-13 | 2700 |
| 2 | First | 10% PCL (M$_n$ = 80 KDa) in Chloroform/DMF 80/20 (by weight) | 1 | 1300 |
|  | Second | 4% PEO (M$_w$ = 600 KDa) in Ethanol/water 40/60 (by weight) | 11-13 | 2700 |
| 3 | First | 10% PCL (M$_n$ = 80 KDa) in Chloroform/DMF 90/10 (by weight) | / | / |
|  | Second | 9% PVA (Mw = 100 KDa) in Ethanol/water 50/50 (by weight) | 22 | 2000 |
| 4 | First | PCL:PEG (9:2 by weight) [M$_n$ (PCL) = 80 KDa; M$_n$ (PEG) = 6 KDa] in Chloroform/DMF 80/20 (by weight) |  |  |
|  | Second | 4% PEO (M$_w$ = 600 KDa) in DMF | 3.2 | 1400 |
| 5 | First | 10 % PCL in CHCl$_3$/DMF 8:2 | 1 | 1300 |
|  | Second | 4% PEO (M$_w$ = 600 KDa) in Ethanol/water 40/60 (by weight) 1 ml PEO solution +50 ml PBS | 200 | 2700 |

Table 3: Shear viscosities of the solutions were measured at different shear rates using a Couette viscometer (Brookfield DVII programmable viscometer). The reported values are the results of extrapolation to zero shear rates. Conductivity was measured with an Oyster conductivity/temperature meter.

Electrospinning—Hollow microtubes (core-shell hollow fibers) were fabricated by a co-electrospinning process using the set up described by Sun et al. 2003 and Zussman et al. 2006 with the polymeric solutions (for forming the shell and coat over the internal surface of the shell) as described in Table 3 above. All experiments were conducted at room temperature (about 22° C.) and a relative humidity of about 55%. The spinning parameters were as follow: the electrostatic field used was approximately 0.44 kV/cm and the distance between the spinneret and collector plate was 16 cm. The flow rates of both the core and shell solutions were controlled by two syringe pumps and were 3.5 ml/hour for the shell solution and 1 ml/hour for the core solution. The fibers were collected as a strip on the edge of a vertical rotating wheel (Theron A., et al., 2001) having a velocity of 1.2 m/second. For fluorescence microscopy, a few fibers were collected directly onto a microscope slide.

Filling of microtubes with diagnostic molecules—An aqueous based droplet (2 μl) with 2% rhodamine was placed near the microtube and following 2 minutes the microtubes were viewed using a fluorescent microscope.

Imaging—Images of the fibers were obtained using a Leo Gemini high resolution scanning electron microscope (HRSEM) at an acceleration voltage of 3 kV and a sample to detector distance of 3-5 mm. The specimens were coated with a thin gold film to increase their conductivity. Fluorescence microscope Leica DM IRE2 at excitation of 514 nanometer (nm), was used for the imaging of fibers filled with fluorescent product.

Example 1

Microfluidic Network for Targeted Delivery of a Medicament of a Diagnostic Agent A microfluidic networks made of microtubes generated by co-electrospinning of biocompatible polymers was prepared as described under "General Materials and Experimental Methods" hereinabove.

Production of a microtube from PCL and PEO (biocompatible polymers)—Co-electrospinning was performed as described above using the following polymeric solutions: The first polymeric solution (for forming the shell) was 10% PCL in CHCL$_3$/DMF (8:2, weight/weight), at a flow rate of 4 ml/hour. The second polymeric solution (for forming the coat over the internal surface of the shell) was 4% PEO in H2O/ethanol (6:4, weight/weight), at a flow rate of 0.5 ml/hour. Co-electrospinning was performed at a voltage (V) of 8.5 kV, and in an electrostatic field of 0.43 kV/cm. The resulting fiber was hollow (i.e., a microtube) with an outer radius (R) of 6-9 μm and a shell thickness (d) of 0.5-2 μm. The plurality of microtubes formed a network resembling a capillary network (FIGS. 1a-b).

Attachment of a microtube network to a coupling element—The inlet network is connected with a Teflon medical tube (SCI Scientific Commodities Inc., I.D. 0,036", and 0.066" O.D.). The network was slightly inserted into the Teflon tube and sealed with an adhesive (Pattex N27, Henkel adhesives). The microtubes are oriented and attached together forming a strand.

Filling the microtube network with a fluid containing a diagnostic agent—An aqueous based droplet (2 μl) containing 2% rhodamine was placed close to the network inlet. Due to capillary rise, the aqueous solution flows along the capillary and reaches the outlet of the capillary which was located about 5 cm far from the inlet. The solution reached the outlet of the capillary within 8-16 minutes with an average velocity of 50-100 micrometer/second. A florescence image of a few capillaries is presented in FIG. 2.

Altogether, these results demonstrate, for the first time, a delivery apparatus for a medicament or a diagnostic agent, using microtubes generated by electrospinning of biocompatible polymers which can be safely implanted in a subject in need thereof.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. D. H. Reneker, A. L. Yarin, E. Zussman, H. Xu, Advances in Applied Mechanics 2006, 40.
2. S. Ramakrishna, K. Fujihara, W.-e. Teo, Lim, T. C., Z. Ma, An Introduction to Electrospinning and Nanofibers, 1 ed., World Scientific Publishing Company, 2005.
3. D. Li, Y. N. Xia, Advanced Materials 2004, 16, 1151.
4. M. Bognitzki, H. Hou, M. Ishaque, T. Frese, M. Hellwig, S. C., A. Schaper, J. H. Wendorff, A. Greiner, Adv. Mater. 2000, 12, 637.
5. R. A. Caruso, J. H. Schattka, A. Greiner, Adv. Mater. 2001, 13, 1577.
6. Z. Sun, E. Zussman, A. L. Yarin, J. H. Wendorff, A. Greiner, Adv. Mater. 2003, 15, 1929.
7. J. H. Yu, S. V. Fridrikh, G. C. Rutledge, Adv. Mater. 2004, 16, 1562.
8. Z. M. Huang, C. L. He, A. Yang, Y. Zhang, X. J. Han, J. Yin, Q. Wu, J. Biomedical Mterials Research, Part A 2006, 77A, 169.
9. H. Jiang, Y. Hu, Y. Li, P. Zhao, K. Zhu, W. Chen, J. Control. Release 2005, 108, 237.
10. Y. Z. Zhang, X. Wang, C. T. Lim, S. Ramakrishna, Biomacromolecules 2006, 7, 1049.
11. D. Li, Y. Xia, Nano Letters 2004, 4, 933.
12. D. Li, J. T. McCann, Y. Xia, Small 2005, 1, 83.
13. E. Zussman, A. L. Yarin, V. Bazilevsky, R. Avrahami, M. Feldman, Adv. Mater. 2006, 18, 348.
14. S, N. Reznik, A. L. Yarin, E. Zussman, L. Bercovici, Physics of Fluids 2006, 18, 1.
15. D. Li, J. T. McCann, Y. Xia, J. Am. Ceram. Soc. 2006, 89, 1861.
16. I. G. Loscertales, A. Barrero, I. Guerrero, R. Cortijo, M. Marquez, A. M. Ganan-Calvo, Science 2002, 295, 1695.
17. I. G. Loscertales, A. Barrero, M. Marquez, R. Spretz, R. Velarde-Ortiz, G. Larsen, Journal of the American Chemical Society 2004, 126, 5376.
18. U.S. Pat. Appl. No. 20060142466 to Tour J. M. et al.
19. US patent application No. 20060119015 to Wehrspohn R., et al.
20. PCT/IB2007/054001 to Zussman et al.

What is claimed is:

1. A kit for delivering a medicament or a diagnostic agent, comprising:
    (i) a coupling element, and;
    (ii) an infusion microtube which comprises an electrospun shell and an electrospun coat over an internal surface of said shell, wherein said electrospun shell and said electrospun coat are each composed of a polymer.

2. A kit for delivering a medicament or a diagnostic agent, comprising:
    (i) a reservoir which comprises the medicament, and;
    (ii) an infusion microtube which comprise an electrospun shell and an electrospun coat over an internal surface of said shell, wherein said electrospun shell and said electrospun coat are each composed of a polymer.

3. A method of delivering a medicament or a diagnostic agent to a subject in need thereof, comprising:
    (a) introducing a microtube configured to deliver the medicament or the diagnostic agent into the subject, said microtube comprises an electrospun shell and an electrospun coat over an internal surface of said shell, wherein said electrospun shell and said electrospun coat are each composed of a polymer; and
    (b) administering the medicament or the diagnostic agent through said microtube,
    thereby delivering the medicament or the diagnostic agent to the subject.

4. The method of claim 3, wherein said microtube is attached to a coupling element.

5. The method of claim 3, wherein said microtube is connected to a reservoir which comprises the medicament or the diagnostic agent.

6. The method of claim 5, wherein said reservoir is connected to a pump.

7. The method of claim 5, wherein said reservoir is connected to or comprises a filter.

8. The method of claim 5, wherein said reservoir is connected to said coupling element.

9. The method of claim 3, wherein said microtube is produced by co-electrospinning two polymeric solutions through co-axial capillaries, wherein a first polymeric solution of said two polymeric solutions is for forming a shell of the microtube and a second polymeric solution of said two polymeric solutions is for forming a coat over an internal surface of said shell, said first polymeric solution is selected solidifying faster than said second polymeric solution and a solvent of said second polymeric solution is selected incapable of dissolving said first polymeric solution.

10. The method of claim 9, wherein a solvent of said first polymeric solution evaporates faster than a solvent of said second polymeric solution.

11. The method of claim 3, wherein said introducing is effected by implanting said microtube in a subject in need thereof.

12. The method of claim 11, wherein said implanting is effected at or in proximity to a tissue-of-interest.

13. The method of claim 5, wherein said reservoir is an implantable reservoir.

14. The method of claim 5, wherein said reservoir is attached on a skin of the subject in need thereof.

15. The method of claim 3, wherein said electrospun shell is formed of a first polymeric solution and said electrospun coat is formed of a second polymeric solution.

16. The method of claim 15, wherein said first polymeric solution solidifies faster than said second polymeric solution.

17. The method of claim 15, wherein a solvent of said second polymeric solution is incapable of dissolving said first polymeric solution.

18. The method of claim 3, wherein a thickness of said shell is from about 100 nm to about 20 micrometer.

19. The method of claim 3, wherein an internal diameter of said microtube is from about 50 nm to about 20 micrometer.

20. The method of claim 3, wherein said shell comprises pores.

21. The method of claim 3, wherein said microtube comprises a length of about 5-20 centimeters (cm).

22. The method of claim 3, wherein said microtube comprises a plurality of microtubes.

23. The method of claim 22, wherein said plurality of microtubes are attached to a coupling element.

24. The method of claim 22, wherein said plurality of microtubes are connected to a reservoir which comprises the medicament or the diagnostic agent.

25. A kit for delivering a medicament or a diagnostic agent, comprising:
   (i) a coupling element, and;
   (ii) an infusion microtube which comprises an electrospun shell and an electrospun coat over an internal surface of said shell, wherein said electrospun shell and said electrospun coat are each composed of a polymer, and wherein said shell comprises pores.

26. A kit for delivering a medicament or a diagnostic agent, comprising:
   (i) a reservoir which comprises the medicament, and;
   (ii) an infusion microtube which comprise an electrospun shell and an electrospun coat over an internal surface of said shell, wherein said electrospun shell and said electrospun coat are each composed of a polymer, and wherein said shell comprises pores.

27. A method of delivering a medicament or a diagnostic agent to a subject in need thereof, comprising:
   (a) introducing a microtube configured to deliver the medicament or the diagnostic agent into the subject, said microtube comprises an electrospun shell and an electrospun coat over an internal surface of said shell, wherein said electrospun shell and said electrospun coat are each composed of a polymer, and wherein said shell comprises pores; and
   (b) administering the medicament or the diagnostic agent through said microtube,
   thereby delivering the medicament or the diagnostic agent to the subject.

28. A method of delivering a medicament or a diagnostic agent to a subject in need thereof, comprising:
   (a) co-electrospinning two polymeric solutions through co-axial capillaries, wherein a first polymeric solution of said two polymeric solutions is for forming a shell of the microtube and a second polymeric solution of said two polymeric solutions is for forming a coat over an internal surface of said shell, said first polymeric solution is selected solidifying faster than said second polymeric solution and a solvent of said second polymeric solution is selected incapable of dissolving said first polymeric solution, and
   (b) introducing said microtube resultant of step (a) into the subject, wherein said microtube is configured to deliver the medicament or the diagnostic agent; and
   (c) administering the medicament or the diagnostic agent through said microtube,
   thereby delivering the medicament or the diagnostic agent to the subject.

* * * * *